United States Patent [19]

Matsumoto et al.

[11] Patent Number: 4,960,568
[45] Date of Patent: Oct. 2, 1990

[54] OXYGEN ANALYZER

[75] Inventors: Yoshiro Matsumoto, Funabashi; Akira Makihara, Ichikawa, both of Japan

[73] Assignee: Osaka Sanso Kogyo Ltd., Osaka, Japan

[21] Appl. No.: 244,206

[22] Filed: Sep. 14, 1988

[30] Foreign Application Priority Data

Oct. 2, 1987 [JP] Japan .................................. 62-151482

[51] Int. Cl.⁵ ............................................. G01N 31/00
[52] U.S. Cl. ........................................ 422/83; 73/23.2;
422/93; 422/103; 436/136; 436/181
[58] Field of Search .................. 422/93, 83, 103, 94;
137/599, 599.1; 73/23, 23.1, 155; 128/205.26;
55/68, 88; 350/266; 204/409; 436/178, 136,
181; 251/335.2

[56] References Cited

U.S. PATENT DOCUMENTS

| | | | |
|---|---|---|---|
| 3,727,623 | 4/1973 | Rabbins | 137/599 X |
| 3,795,260 | 3/1974 | Bergson | 137/599 |
| 3,874,636 | 4/1975 | Bake et al. | 251/335.2 |
| 4,098,303 | 7/1978 | Gammell | 141/52 |
| 4,219,530 | 8/1980 | Kopp et al. | 422/101 X |
| 4,635,735 | 1/1987 | Crownover | 175/48 |
| 4,750,709 | 6/1988 | Kolenc et al. | 251/335.2 |
| 4,760,990 | 8/1988 | Kerger et al. | 251/335.2 |

FOREIGN PATENT DOCUMENTS 17249  10/1980  European Pat. Off. ......... 137/599.1

Primary Examiner—Robert J. Warden
Assistant Examiner—Jill Johnston
Attorney, Agent, or Firm—Robert I. Pearlman; Carol A. Nemetz; David M. Rosenblum

[57] ABSTRACT

An improved oxygen analyzer device is disclosed which comprises a gas flow passage having inlet and exhaust ports, an oxygen concentration detector in proximity to the exhaust port and first and second parallel intermediate flow passages, one of which contains a purifier to remove oxygen from the gas flowing therethrough. The device is characterized by the use of metal, diaphram-type, three-way valves in the branch-off and junction points between the intermediate flow passages. The valves eliminate dead space in conventional devices that extends both the calibration and analysis time of such devices.

3 Claims, 1 Drawing Sheet

OXYGEN ANALYZER

This invention relates to a device for analyzing oxygen in a gas mixture characterized by a sampling line with an extremely small dead zone and a smaller sampling space.

BACKGROUND OF THE INVENTION

In an increasing number of applications of various gases industry, the purity of the gas is a critical criteria in achieving the desired result. A good example of such applications is the use of inerting atmospheres, such as nitrogen or argon, in the processing of semiconductor devices. In such applications, it is necessary to monitor the gas being utilized for the presence of contaminant gases.

In many industrial applications, particularly those utilizing an inerting atmosphere, such as nitrogen or argon, it is necessary to monitor the level of oxygen present as a contaminant in the atmosphere and maintain it within prescribed limits. In other applications requiring a controlled atmosphere, it is necessary to monitor the level of oxygen so that it is within a certain range in the environment of, e.g. the furnace.

It will be appreciated, therefore, that there is a need for an efficient, accurate oxygen analyzer Such a device is provided in accordance with this invention.

SUMMARY OF THE INVENTION

An oxygen analyzer comprising a gas flow passage having a gas inlet port at one end and a gas exhaust port at the opposite end, an oxygen concentration detector means in proximity to the exhaust port, the gas flow passage between the inlet port and the oxygen concentration detector means comprising two parallel, intermediate flow passages and a purifier provided at an intermediate point of a first of the intermediate passages. Calibration of the oxygen detector is effected by flowing the gas to be tested through only the first of the intermediate passages containing the purifier. The oxygen concentration of the gas to be measured is then determined by flowing it through only the second of the intermediate flow passages, the devices being characterized by having metal, diaphram-type, three-way valves to regulate the flow of gas through the intermediate flow passages.

DESCRIPTION OF THE PREFERRED EMBODIMENTS

Figure 1:
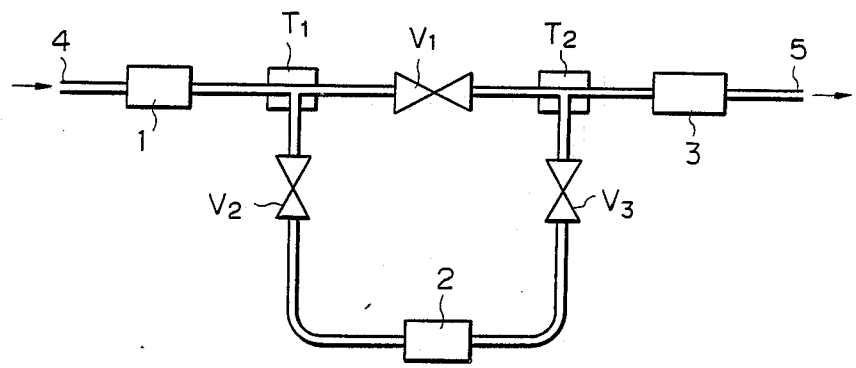
FIG. 1 is a block diagram of a conventional oxygen analyzer.

A conventional oxygen analyzer is illustrated in FIG. 1. In FIG. 1, a flow regulator 1 regulates the flow of a gas to be analyzed which enters the analyzer through inlet port 4. In FIG. 1, the path of the flow of gas is governed by tees T1 and T2 and stop conventional valves V1, V2 and V3. Purifer 2 contains a conventional oxygen scavenger which effectively removes oxygen from the gas passing therethrough. Gas passing through purifier 2 is free of oxygen and is therefore termed a zero gas. Detector means 3 is a conventional analyzer having the capacity to determine low levels of oxygen in the gas passing therethrough.

In operation, the detector means 3 in FIG. 1 is initially calibrated by closing stop valve V1, opening stop valves V2 and V3 and allowing the gas to be detected to flow through the flow regulator 1, the tee T1, the purifier 2, the tee T2 and the detector means 3. The gas exits the device through exhaust port 5. There is thus established a calibration line and the detector means 3 is calibrated utilizing the zero gas exiting the purifier 2.

Upon completion of the calibration of the detector means 3, stop valves V2 and V3 are closed and stop valve V1 is opened thereby allowing the gas to be measured to flow through a measurement line consisting of the flow regulator, tees T1 and T2, stop valve V1 and detector means 3 whereby the oxygen content thereof is determined.

It will be apparent that, in the changeover from calibration line to the measurement line of the device illustrated in FIG. 1, a dead zone is created between the stop valves V1, V2 and V3 and tees T1 and T2. For example, when calibration is started by opening the calibration line, zero gas flowing from the purifer 2 will be mixed with oxygen-containing gas in the dead space between stop valve V1 and tee T2 thereby reducing the purity of the zero gas.

As a result of the mixing of the gas in the dead zone with the zero gas, it will take some time before the purity of the zero gas, which is the calibration gas for the system, becomes stable since the gas in the dead zone does not readily flow therefrom. A similar effect occurs during the measurement phase of the device operation since there is zero gas in the dead zone between stop valve V3 and tee T2. As a result thereof, appreciable time is required before the detector means 3 can properly measure the oxygen content of the gas entering port 4.

It is also possible for air to enter the dead zone formed between the tee T1 and the stop valve V2 during changing of the gas to be measured which has a negative influence on the operation of the device.

Figure 2:
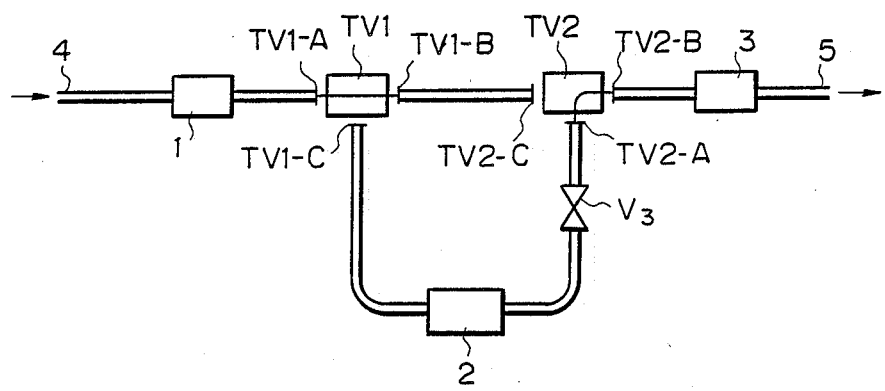
FIG. 2 is a block diagram of an improved oxygen analyzer according to the present invention.
Figure 3:
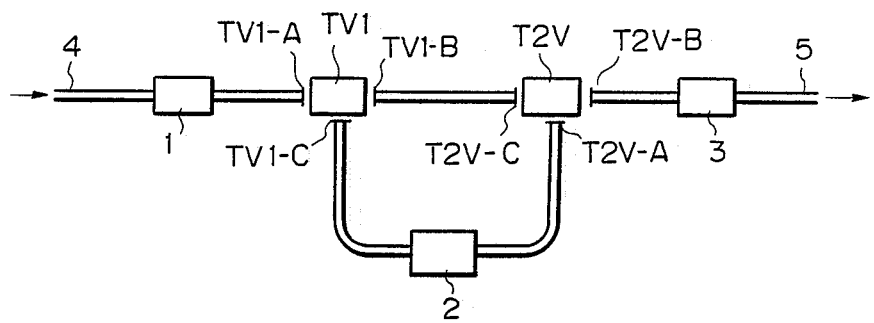
FIG. 3 is a block diagram of an alternative embodiment of the analyzer illustrated in FIG. 2.

In contrast to the prior art device illustrated in FIG. 1, embodiments of the improved oxygen analyzer of the present invention are illustrated in FIGS. 2 and 3. The inlet and exhaust ports, the flow regulator, the purifier and the detector means carry the same designations in FIGS. 2 and 3 as in FIG. 1 and perform the same functions. In FIG. 2, stop valve V3 is situated as in FIG. 1 and performs the same function.

The embodiment of the present invention illustrated in FIG. 2 differs from the prior art device shown in FIG. 1 in that stop valves V1 and V2 and tees T1 and T2 are replaced with metal, diaphram-type, three-way valves TV1 and TV2. This type of valve has been found to be very well suited for analyzing extremely small amounts of gas, such as is required in the subject oxygen analyzer, since it is possible to close the valve securely by strongly pressing the valve body against the valve seat. The metal diaphram-type three-way valve is advantageous over a ball valve-type three-way valve which inherently has a dead zone between the ball and the main body.

Referring to FIG. 2, the valves utilized in the embodiment illustrated therein are constructed such that, only two of the three ports are in communication when the valve is in the closed position and all three ports are in communication when the valve is in the open position. Thus, with both valves in the closed position, ports TV1-A and TV1-B are in communication in valve TV1 with port TV1-C being cut off from communication and ports TV2-A and TV2-B are in communication with port TV2-C being cut off from communication.

With three-way valve TV2 remaining closed so that port TV2-C blocks the measurement line, three-way valve TV1 and stop valve V3 are opened, thus establishing the calibration line as described above with reference to FIG. 1. In the embodiment of the present invention illustrated in FIG. 2, the dead zone between the stop valve V1 and the tee T2 present in the calibration line of the conventional analyzer shown in FIG. 1 is eliminated, thus enabling more rapid zero calibration of the detector 3.

Closing the three-way valve TV1 and the stop valve V3 interrupts the calibration line at both the port TV1-C and the stop valve V3. The measurement line is established by opening the three-way valve TV2, thus placing ports TV2-B and TV2-C in communication between the stop valve V1 and the tee T2 present in the calibration line of the conventional analyzer shown in FIG. 1 is eliminated, thus enabling a more rapid accurate measurement of the gas flowing directly into the detector 3.

In this case, the dead zone between the tee T1 and the stop valve V2 in the conventional analyzer shown in FIG. 1 is eliminated, whereby more rapid measurement of the oxygen concentration of the newly introduced gas is achieved, even if the gas to be measured is changed from one type of gas to another. The dead zone between the tee T2 and the stop valve V3 present in the conventional analyzer is still present in the embodiment of FIG. 2 as a dead zone between the three-way valve TV2 and the stop valve V3. However, the dead zone has little influence upon achievement of proper measurement. In other words, the gas retained in the dead zone does not appreciably affect the value of the oxygen concentration detected by the detector 3, even if the retained zero gas becomes part of the gas to be measured. This is because the gas to be measured is usually of high purity and the amount of the gas to be measured which flows through the measurement line is far larger than the zero gas retained in the dead zone.

FIG. 3 is a block diagram showing a second embodiment of the oxygen analyzer of the present invention This second embodiment differs from that illustrated in FIG. 2 in that the stop valve V3 is not present and the metal diaphram-type three-way valve TV2, downstream of the purifier, in the first embodiment is replaced with a dual-type, metal, diaphram three-way valve T2V.

Although the dual-type metal diaphram three-way valve T2V in FIG. 3 is basically similar in structure to that of the three-way valves TV1, TV2, it has two positions by which communication between the ports T2V-A and T2V-B and between the ports T2V-C and T2V-B is alternately established. It is thus possible to eliminate the dead zone between the three-way valve TV2 and the stop valve V3 present in the embodiment illustrated in FIG. 2. Although the effect of the dead zone present between the three-way valve TV2 and the stop valve V3 in FIG. 2 is considered negligible in most situations, it cannot be overlooked when the gas to be measured contains a high oxygen concentration and the gas retained in the dead zone will have an influence on the gas to be measured. Thus, the embodiment of the present invention illustrated in FIG. 3 is particularly suited for measurement of a gas of a high oxygen concentration.

Referring to FIG. 3, when the three-way valve TV1 and the first position of the dual-type three-way valve T2V are open so that ports T2V-A and T2V-B are brought into communication, the measurement line is cut off at the port T2V-C, while the calibration line is established through-out the passage, whereby calibration can be effected. In this case, there is no dead zone anywhere throughout the passages. Thereafter, the three-way valve TV1 is closed and the dual-type three-way valve T2V is in the second position, the measurement line is established throughout the passage, while the calibration line is cut off at two points, i.e. the ports of TV1-C and T2V-A. As in the previous case, there is no dead zone anywhere throughout the passages.

The oxygen analyzer according to the present invention substantially reduces dead zones along the length of the calibration line and the measurement line, whereby the zero calibration of the detector 3 can be rapidly achieved so that an accurate measurement is, in turn, possible within a short period of time after the commencement of measurement. In addition, the oxygen analyzer of the present invention requires fewer components as compared with conventional ones, thus making it possible to make the sampling space smaller. The device of the present invention may be used as a sampling flow for other analyzing apparatus.

The invention has been described with reference to preferred embodiments thereof. It will be appreciated by those skilled in the art that various modifications may be made from the specific details given without departing from the spirt and scope of the invention.

What is claimed is:

1. An oxygen concentration analyzer comprising:
a gas flow passage having a gas inlet port at one end thereof for connecting a gas source to the gas flow passage in an atmospheric environment and a gas exhaust port at the opposite end for discharging a gas from the gas flow passage;
an oxygen concentration detector disposed in the gas flow passage in proximity to the gas exhaust port;
a portion of the gas flow passage between the gas inlet port and the oxygen concentration detector comprising first and second intermediate flow passages positioned to provide parallel intermediate flow paths for the gas to the oxygen concentration detector and connected to the gas inlet port via a branch-off point and connected to the oxygen concentration detector via a junction point;
a purifier disposed in the first intermediate flow passage for removing oxygen from the gas flowing therethrough;
first and second metal diaphragm type three-way valves, positioned at the branch-off point and junction point between the first and second intermediate flow passages and each of said first and second three-way valves respectively having a set of first, second, and third ports connected to the inlet port and the first and second intermediate flow passages and a set of fourth, fifth, and sixth ports connected to the oxygen concentration detector and the first and second intermediate flow passages;
the first and second three-way valves designed to be selectively switchable between two positioned in which in a first of the positions, the first, second, fourth, and fifth ports of each of the first and second three-way valves are opened to allow the gas to flow through the first intermediate flow passage and the sixth port of the second three-way valve is closed to prevent the flow of gas in the second intermediate flow passage, and in which in a second of the positions, the first, third, fourth, and sixth ports of each of the first and second three-way valves are opened so that gas may flow through the second intermediate flow passage and the second port of the first three-way valve is closed to prevent the flow of gas in the first intermediate flow passage;

whereby, when the first and second three-way valves are set in the first of the positions and gas flows through the purifier before introduction into the oxygen concentration detector to calibrate the oxygen concentration detector and the second intermediate flow passage is blocked off at the junction point to prevent the contamination of the gas after the removal of oxygen therefrom with the gas in the second intermediate flow passage and when the first and second three-way valves are set in the second of the positions, the gas flows directly into the oxygen concentration detector to detect the oxygen content thereof and the first intermediate flow passage is blocked at the branch-off point to alternately allow the gas source to be connected to the inlet port without air entering the second intermediate flow passage and eventually contaminating the gas passing through the purifier and used in calibrating the oxygen concentration detector.

2. An oxygen concentration analyzer according to claim 1, further comprising a stop valve positioned in said first intermediate flow passage between the purifier and the second three-way valve, the stop valve being selectively switchable between an open position when the first and second three-way valves are set in the first of the positions and a closed position when the first and second valves are set in the second of the positions.

3. An oxygen concentration detector according to claim 1, wherein the fifth port of the second three-way valve is closed when it is set in the second of the positions to prevent the contamination of the gas to be detected flowing through the second intermediate flow passage with the gas in the first intermediate flow passage, the oxygen having been removed therefrom by the purifier.

* * * * *

UNITED STATES PATENT AND TRADEMARK OFFICE
CERTIFICATE OF CORRECTION

PATENT NO. : 4,960,568
DATED : October 2, 1990
INVENTOR(S) : Yoshiro Matsumoto and Akira Makihara It is certified that error appears in the above-indentified patent and that said Letters Patent is hereby corrected as shown below:

Column 5, line 13: replace "and" and insert --the--

Signed and Sealed this

Fourteenth Day of December, 1993

Attest:

BRUCE LEHMAN

Attesting Officer         Commissioner of Patents and Trademarks